United States Patent
Saito (10) Patent No.: US 10,881,361 B2
(45) Date of Patent: Jan. 5, 2021

(54) RADIOGRAPHIC IMAGING APPARATUS

(71) Applicant: Shimadzu Corporation, Kyoto (JP)

(72) Inventor: Atsuo Saito, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/495,986

(22) PCT Filed: Apr. 3, 2017

(86) PCT No.: PCT/JP2017/013890
§ 371 (c)(1),
(2) Date: Sep. 20, 2019

(87) PCT Pub. No.: WO2018/185802
PCT Pub. Date: Oct. 11, 2018

(65) Prior Publication Data
US 2020/0046304 A1  Feb. 13, 2020

(51) Int. Cl.
*A61B 6/04* (2006.01)
*A61B 6/00* (2006.01)

(52) U.S. Cl.
CPC .......... *A61B 6/0407* (2013.01); *A61B 6/4441* (2013.01); *A61B 6/462* (2013.01); *A61B 6/548* (2013.01); *A61B 6/465* (2013.01)

(58) Field of Classification Search
None
See application file for complete search history.

(56) References Cited

U.S. PATENT DOCUMENTS

| 4,972,852 | A | * | 11/1990 | Koob | A61B 5/04004 600/415 |
| 4,977,588 | A | * | 12/1990 | Van der Ende | A61B 6/4405 378/17 |
| 5,474,068 | A | * | 12/1995 | Takamori | A61B 6/56 242/378.2 |
| 7,015,478 | B2 | * | 3/2006 | Yamamoto | A61B 6/544 250/370.09 |
| 8,516,636 | B2 | * | 8/2013 | Gagnon | A61B 5/0555 5/601 |

(Continued)

FOREIGN PATENT DOCUMENTS

JP  2015-150055 A  8/2015

OTHER PUBLICATIONS

International Search Report for PCT application No. PCT/JP2017/013890, dated May 30, 2017, submitted with a machine translation.

*Primary Examiner* — Thomas R Artman
(74) *Attorney, Agent, or Firm* — Muir Patent Law, PLLC (57) ABSTRACT

A storage unit 2 arranged on a foot side of a subject placed on a top board is provided with a box composed of a block member 22 and a plate member 23 and a lid 21 covering an upper side of the box. The lid 21 is provided so as to be capable of pivoting about a shaft 20 relative to the plate member 23 of the box composed of the block member 22 and the plate member 23. When the lid 21 is in a closed state, the upper portion of the plate member 23 of the box composed of the block member 22 and the plate member 23 is covered by the lid 21. In this state, as shown in FIG. 2, the upper surface of the lid 21 and the surface of the top board of the storage unit 2 are arranged at the same height, and are thus coplanar.

6 Claims, 6 Drawing Sheets

(56) References Cited

U.S. PATENT DOCUMENTS

| | | | | |
|---|---|---|---|---|
| 8,723,131 | B2* | 5/2014 | Kobayashi | G03B 42/02 |
| | | | | 250/370.09 |
| 9,892,233 | B2* | 2/2018 | Zeilinger | A61B 6/467 |
| 10,667,784 | B2* | 6/2020 | Gille | A61B 5/02007 |
| 2001/0003218 | A1* | 6/2001 | Schaefer | A61B 6/0487 |
| | | | | 5/601 |
| 2006/0225211 | A1* | 10/2006 | Verhoeven | A61B 6/56 |
| | | | | 5/601 |
| 2007/0055145 | A1* | 3/2007 | Zelnik | A61B 6/04 |
| | | | | 600/428 |
| 2007/0232933 | A1* | 10/2007 | Gille | A61B 8/467 |
| | | | | 600/481 |
| 2010/0301223 | A1* | 12/2010 | Kobayashi | G03B 42/02 |
| | | | | 250/370.08 |
| 2012/0265077 | A1* | 10/2012 | Gille | A61B 8/565 |
| | | | | 600/463 |
| 2015/0046137 | A1* | 2/2015 | Zeilinger | A61B 6/542 |
| | | | | 703/2 |
| 2016/0158082 | A1* | 6/2016 | Gainor | A61G 13/101 |
| | | | | 5/690 |
| 2020/0046304 | A1* | 2/2020 | Saito | A61B 6/0407 |

* cited by examiner

RADIOGRAPHIC IMAGING APPARATUS

TECHNICAL FIELD

The present invention relates to a radiographic imaging apparatus for performing radioscopy or radiography of a subject on an examination table.

BACKGROUND ART

For example, an X-ray imaging apparatus used for performing an examination procedure and a surgery procedure of a circulatory system is provided with: an examination table equipped with a top board for placing a subject thereon; an X-ray tube; an X-ray detection unit for detecting X-rays irradiated from the X-ray tube and transmitted through the subject on the examination table; a substantially C-shaped arm having an arcuate guide unit and supporting the X-ray tube and the X-ray detection unit; a slide mechanism for slidably supporting the C-shaped arm in a state of being engaged with the arcuate guide unit; and a rotation mechanism for rotatably supporting the C-shaped arm centering on an axis facing the horizontal direction via the slide mechanism. Further, a biplane X-ray imaging apparatus for imaging a subject from two different directions has a configuration in which a pair of C-shaped arms each having an X-ray tube and an X-ray detection unit as described above is provided.

Such an X-ray imaging apparatus is provided with an operation unit for performing moving operations of a C-shaped arm and a top board of an examination table, various X-ray imaging operations, and the like. This operation unit can be attached to the top board of the examination table from a plurality of different directions in response to the arrangement relation between the C-shaped arm and the examination table, the standing position of the operator who operates this operation unit, etc. In Patent Document 1, an X-ray imaging apparatus is disclosed in which an operation unit can be attached to an examination table from three directions.

PRIOR ART

Patent Document

Patent Document 1: Japanese Unexamined Patent Application Publication No. 2015-150055

SUMMARY OF THE INVENTION

Problems to be Solved by the Invention

An operation unit for performing various operations is connected to the examination table via a cable. On the other hand, a top board of the examination table is configured to perform horizontal movements and upward and downward movements relative to the support unit according to the X-ray imaging mode. For this reason, the cable extending from the operation unit provided to the top board has a sufficient length in consideration of the movements of the top board.

Further, as described above, the operation unit can be attached to the top board of the examination table from a plurality of different directions in response to the arrangement relation between the C-shaped arm and the examination table, the standing position of the operator who operates the operation unit, etc. Further, when the subject rides on the top board and gets off the top board, in some cases, the operation unit is temporarily removed from the top board. Also for this reason, the cable extending from the operation unit has a sufficient length.

In this way, the length of the cable extending from the operation unit attached to the top board of the examination table is taken into account the allowance length, so when the slack of the cable occurs, there is a possibility that a subject, etc., gets caught in the cable, resulting in the disconnection of the cable. Also, the slack of the cable is a problem from the viewpoint of cleanliness.

The present invention has been made to solve the aforementioned problems, and aims to provide a radiographic imaging apparatus capable of eliminating slack of a cable even when an operation unit is attached to a top board from a plurality of different directions.

Means for Solving the Problems

According to the invention as recited in claim 1, a radiographic imaging apparatus includes: an examination table; a radiation irradiation unit configured to irradiate radiation to a subject on the examination table; and a radiation detection unit configured to detect the radiation irradiated from the radiation irradiation unit and transmitted through the subject. The examination table is provided with: a top board configured to place the subject thereon; a top board moving mechanism configured to move the top board relative to a support unit; an operation unit capable of being attached to the top board from a plurality of different directions; a box provided to the top board on a foot side of the subject placed on the top board and capable of storing a cable connected to the operation unit; and a lid configured to cover an upper portion of the box.

According to the invention as recited in claim 2, in the invention as recited in claim 1, a hole portion for allowing the cable to pass through is formed in both side surfaces of the box provided to the top board relative to a body axis of the subject.

According to an invention as recited in claim 3, in the invention as recited in claim 2, a winding member capable of winding the cable is provided in the box.

According to an invention as recited in claim 4, in the invention as recited in claim 3, a rail is arranged on both sides of the top board, and the operation unit is attached to the top board via the rail.

According to an invention as recited in claim 5, in the invention as recited in claim 3, the radiographic imaging apparatus further includes: a C-shaped arm having an arcuate guide portion and supporting the radiation irradiation unit and the radiation detection unit; a slide mechanism slidably supporting the C-shaped arm by being engaged with the arcuate guide portion; and a rotation mechanism capable of rotatably supporting the C-shaped arm via the slide mechanism.

Effects of the Invention

According to the invention as recited in claim 1, even in cases where the operation unit is attached to the top board from a plurality of different directions, it is possible to eliminate the slack of the cable by storing the extra length portion of the cable in the box.

According to the invention as recited in claim 2, even in cases where the operation unit is attached on either side of the top board, it is possible to guide the cable into the box through the hole portion.

According to the invention as recited in claim 3, by winding the extra length portion of the cable around the winding member, it becomes possible to store the cable in an organized state in the box.

According to the invention as recited in claim 4, even in cases where the operation unit is arranged in any region of the rails on both sides of the top board, it becomes possible to eliminate the slack of the cable.

According to the invention as recited in claim 5, even in cases where the operation unit is arranged at various positions relative to the top board in accordance with the change of the posture of the C-shaped arm, it is possible to eliminate the slack of the cable.

EMBODIMENTS FOR CARRYING OUT THE INVENTION

Figure 1:
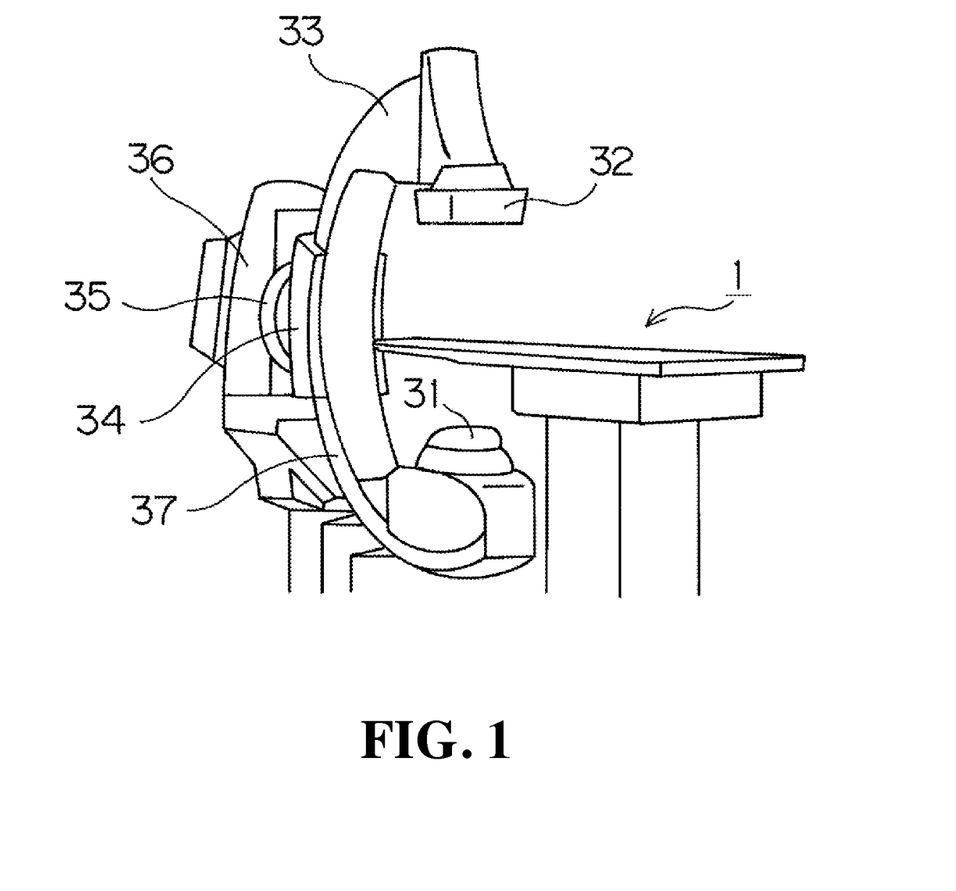
FIG. 1 is a schematic view of an X-ray imaging apparatus as a radiographic imaging apparatus according to the present invention.

Hereinafter, embodiments of the present invention will be described with reference to the drawings. FIG. 1 is a schematic view of an X-ray imaging apparatus as a radiographic imaging apparatus according to the present invention.

This X-ray imaging apparatus is provided with: an X-ray irradiation unit 31 composed of an X-ray tube and a collimator; a flat panel detector 32 as an X-ray detection unit to detect X-rays irradiated from the X-ray irradiation unit 31 and transmitted through the subject lying on the examination table 1; a substantially C-shaped arm 33 for supporting these X-ray irradiation unit 31 and flat panel detector 32; a slide unit 34 for slidably supporting the C-shaped arm 33; a swivel unit 35 for turning the slide unit 34; and a support unit 36 for supporting the swivel unit 35 in a standing state relative to the floor surface.

The C-shaped arm 33 is provided with an arcuate guide portion 37, and the slide unit 34 supports the C-shaped arm 33 in a slidable state by being engaged with the guide portion 37. The C-shaped arm 33 supports the X-ray irradiation unit 31 and the flat panel detector 32 in a state in which the axis of X-rays extended from the focal point of the X-ray tube in the X-ray irradiation unit 31 to the flat panel detector 32 coincides with the diameter of the arc forming the guide portion 37. The swivel unit 35 rotates the slide unit 34 together with the C-shaped arm 33 and the like, centering on the axis orthogonal to the axis of X-rays extending from the focal point of the X-ray tube to the flat panel detector 32. In the X-ray imaging apparatus having such a configuration, by sliding and turning the C-shaped arm 33, X-ray fluoroscopy or X-ray imaging can be performed on the subject on the examination table 1 from any direction.

Figure 2:
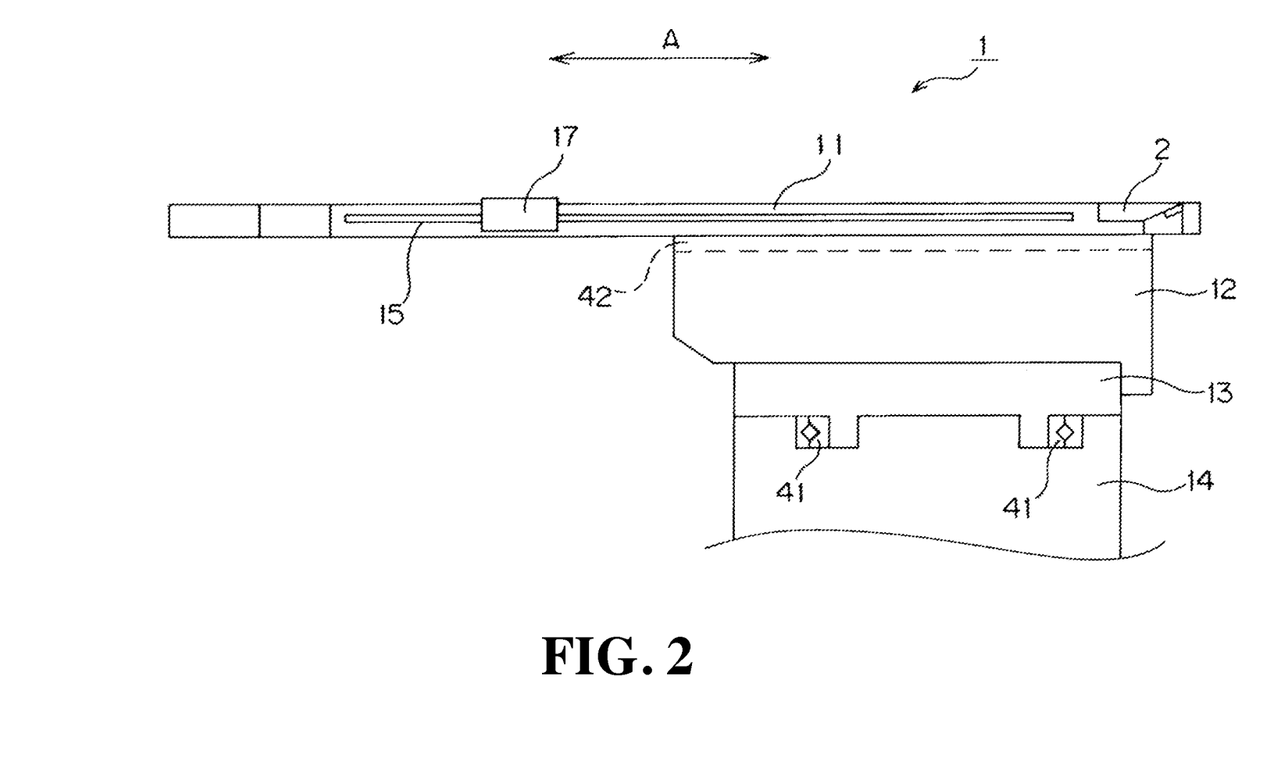
FIG. 2 is a schematic side view of an examination table 1.
Figure 3:
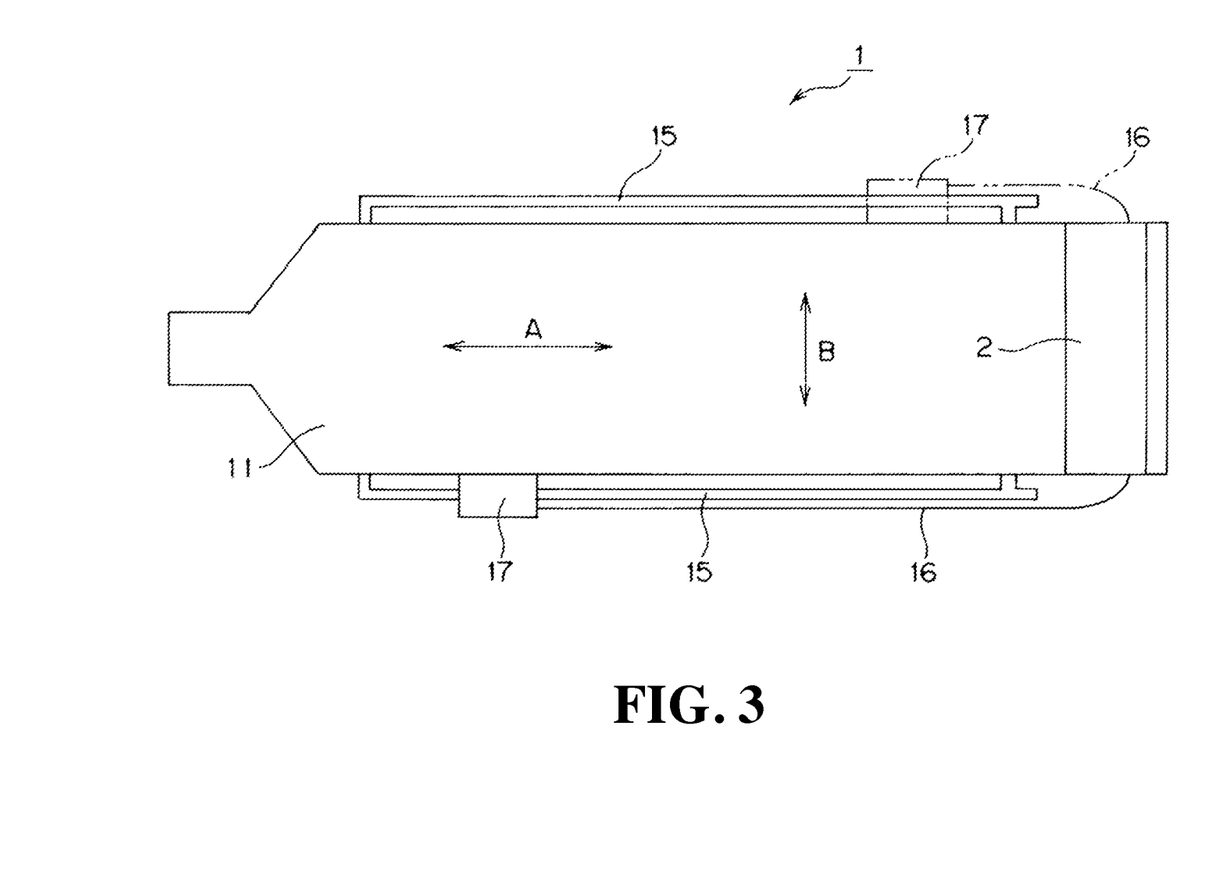
FIG. 3 is a schematic plan view of the examination table 1.

Next, the configuration of the examination table 1 which is a characteristic part of the present invention will be described. FIG. 2 is a schematic side view of the examination table 1. FIG. 3 is a schematic plan view of the examination table 1.

The examination table 1 is provided with a top board 11 configured to place a subject thereon, a first support unit 12, a second support unit 13, and a third support unit 14. The top board 11 is moved forward and backward in the longitudinal direction indicated by the arrow A in FIG. 2 and FIG. 3 relative to the first support unit 12, the second support unit 13, and the third support unit 14 by being guided by a guide member 42. This longitudinal direction is the body axis direction of the subject lying on the top board 11. Note that the subject lies on the top board 11 so that the head side is positioned on a side where the width of the top board 11 is reduced (left side in FIG. 2 and FIG. 3) and the foot side is positioned on the opposite side (right side in FIG. 2 and FIG. 3).

Further, the second support unit 13 is moved forward and backward together with the top board 11 and the first support unit 12 in the short direction indicated by the arrow B in FIG. 3 relative to the third support unit 14 by being guided by guide members 41. This short direction is a direction orthogonal to the above-described longitudinal direction. The first support unit 12 swings together with the top board 11 relative to the second support unit 13 by a swing mechanism (not shown), centering on the axis parallel to the longitudinal direction.

A pair of rails 15 is arranged on both sides of the top board 11 in the short direction (both sides relative to the body axis of the subject placed on the top board 11). The operation unit 17 is detachably attached to the rail 15 at an arbitrary position. That is, the operation unit 17 is attached to the top board 11 via the rail 15. The operation unit 17 is for changing the posture of the C-shaped arm 33, for moving the top board 11 of the examination table 1, or for performing various X-ray imaging operations.

A cable 16 is connected to the operation unit 17. The end portion region of the cable 16 opposite to the operation unit 17 is stored in the storage unit 2 of the cable 16. The cable 16 has a length that allows the operation unit 17 to be attached at any position on the rail 15. That is, the cable 16 has a length that allows the operation unit 17 to be attached to all of the attachment regions where the operation unit 17 is attached to the top board 11 via the rail 15. The storage unit 2 of the cable 16 is provided in a state of being connected to the end portion region of the top board 11 on the foot side (the right side in FIG. 2 and FIG. 3) of the subject placed on the top board 11.

Figure 4:
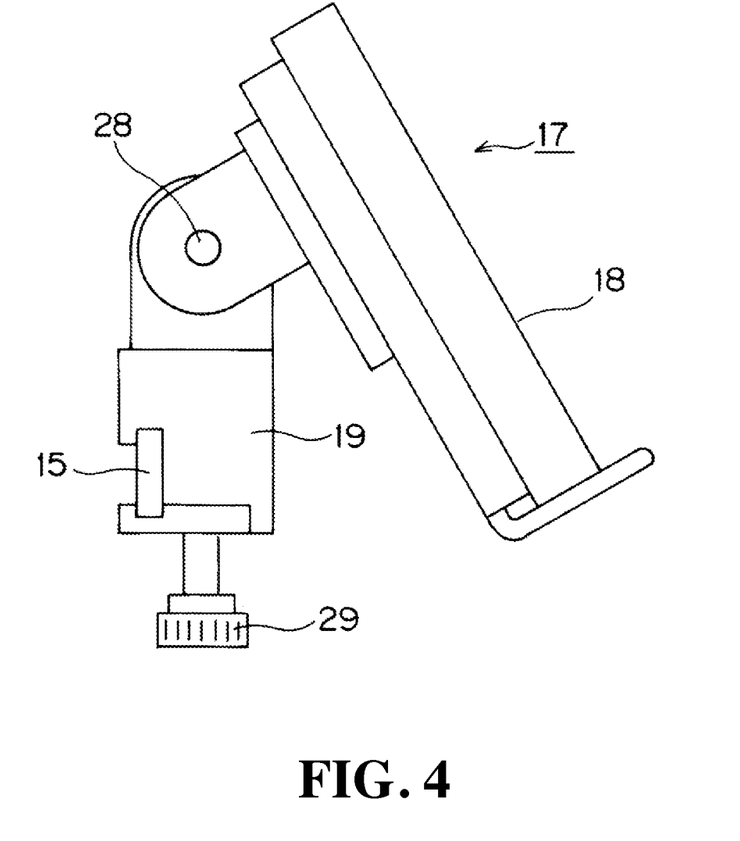
FIG. 4 is a schematic side view showing a state in which an operation unit 17 is attached to a rail 15.

FIG. 4 is a schematic side view showing the state in which the operation unit 17 is attached to the rail 15.

The operation unit 17 is provided with an operation region 18 for performing various operations. In this operation region 18, various operation buttons, touch panel type display unit, etc., are provided. The operation unit 17 is also provided with an operation lever or the like as necessary. The operation unit 17 is arranged so as to be inclinable relative to a support unit 19, centering on a shaft 28. The support unit 19 is attached to the rail 15 using an operation screw 29.

Figure 5:
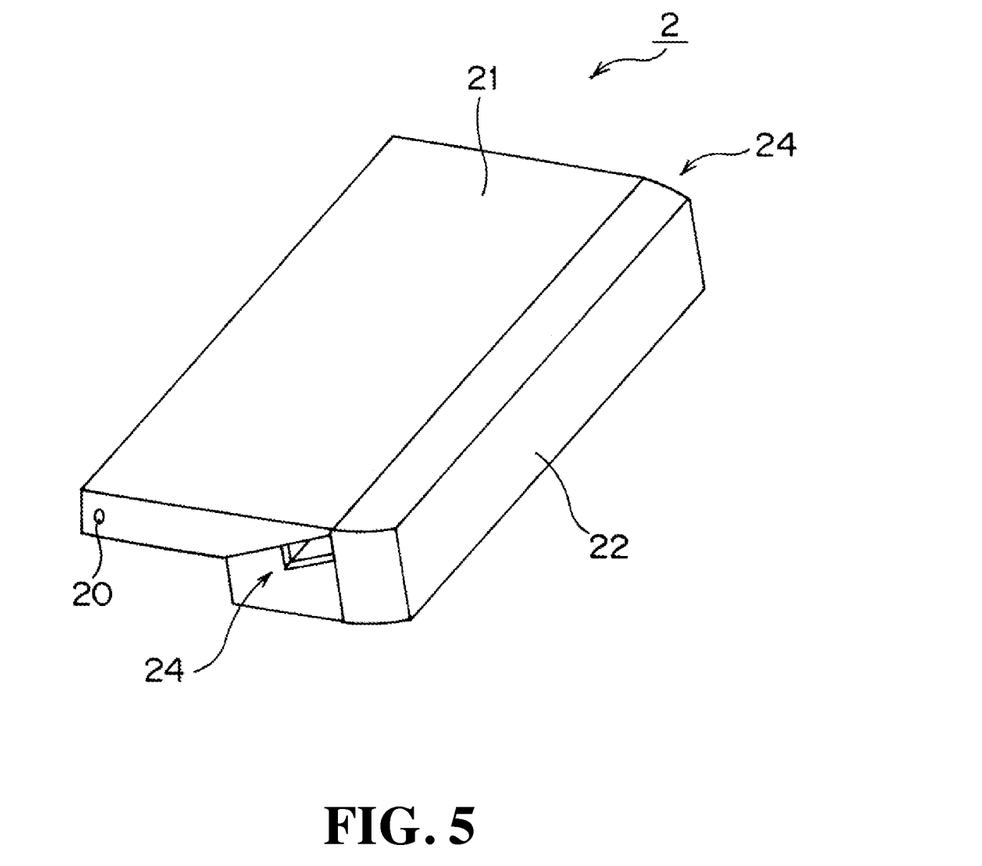
FIG. 5 is a perspective view of a storage unit 2.
Figure 6:
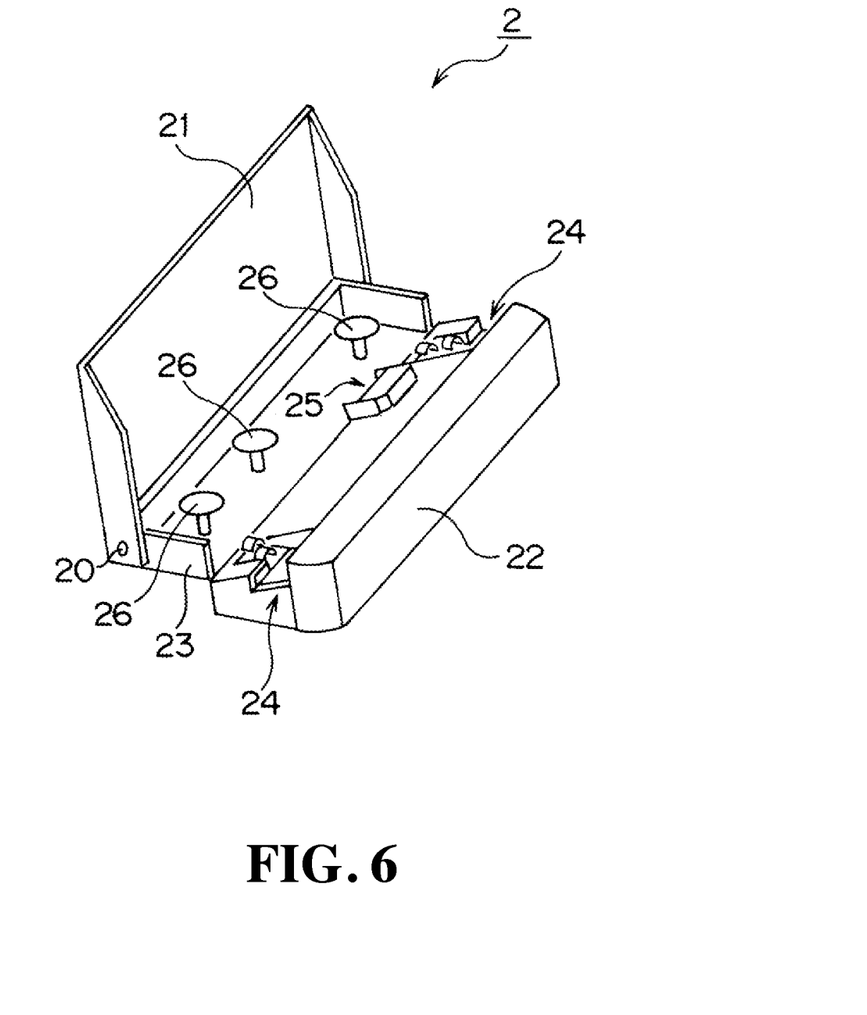
FIG. 6 is a perspective view of the storage unit 2.

FIG. 5 and FIG. 6 are perspective views of the storage unit 2 described above. FIG. 5 shows a state in which the lid 21 of the storage unit 2 is closed, and FIG. 6 shows a state in which the lid 21 of the storage unit 2 is opened.

The storage unit 2 is provided with a box composed of a block member 22 and a plate member 23, and a lid 21 configured to cover the upper portion of the box. The lid 21 is provided so as to be swingable relative to the plate member 23 of the box composed of the block member 22 and the plate member 23, centering on a shaft 20. As shown in FIG. 5, when the lid 21 is in a closed state, the upper portion of the plate member 23 of the box composed of the block member 22 and the plate member 23 is covered by the lid 21. In this state, as shown in FIG. 2, the upper surface of the lid 21 of the storage unit 2 and the surface of the top board 11 are arranged at the same height, and are thus coplanar.

In both side surfaces of the block member 22 constituting the box relative to the body axis of the subject placed on the top board 11 (side surfaces on both sides in the short direction indicated by the arrow B in FIG. 3), a hole portion 24 for allowing the cable 16 connected to the operation unit 17 to pass through is formed. As shown in FIG. 5, the hole portion 24 is open toward the outside even when the lid 21 is in a closed state that covers the box.

As shown in FIG. 6, a hole portion 25 for guiding the cable 16 to the first support unit 12 is formed in the block member 22 constituting the box. Further, the plate member 23 constituting the box is provided with three winding members 26 each capable of winding the cable 16 therearound.

In the X-ray imaging apparatus having the above configuration, corresponding to the arrangement relation between the C-shaped arm 33 and the examination table 1, the standing position of the operator operating the operation unit 17, etc., the operation unit 17 is attached to a predetermined position on one of the pair of rails 15 provided to the top board 11 of the examination table 1. In a state in which the lid 21 of the storage unit 2 is opened, the extra length portion of the cable 16 extending from the operation unit 17 is stored in the box composed of the block member 22 and the plate member 23 of the storage unit 2. At this time, the cable 16 is introduced into the box through one of the hole portions 24 formed in both side surfaces of the block member 22 constituting the box. Then, if necessary, after the extra length portion of the cable 16 is wound around a plurality of winding members 26 among the three winding members 26, the lid 21 is closed.

In this state, since the extra length portion of the cable 16 is stored in the box of the storage unit 2, it is possible to prevent the cable 16 from hanging down. For this reason, the subject, etc., is not caught in the cable 16, the cable 16 is not disconnected, or the cable 16 is not contaminated by the slack of the cable 16. Note that the cable 16 has reached the first support unit 12 shown in FIG. 2 through the hole portion 25 formed in the block member 22 constituting the box. Therefore, even when the top board 11 is configured to move in the longitudinal direction indicated by the arrow A in FIG. 2 and FIG. 3 or in the short direction indicated by the arrow B, the phenomenon that the cable 16 hangs down does not occur.

When the lid 21 of the storage unit 2 is in the closed state, as shown in FIG. 2, the upper surface of the lid 21 of the storage unit 2 and the surface of the top board 11 are arranged at the same height, and are thus coplanar. For this reason, it is possible to place a device or the like used at the time of X-ray imaging on top of the lid 21.

In the above-described embodiment, the case in which the operation unit 17 is attached to the pair of rails 15 provided on both sides of the top board 11 is described. However, for example, a configuration may be adopted in which a rail is further provided to the block member 22 of the storage unit 2 and the operation unit 17 can be attached to the top board 11 from three directions.

Further, in the above-described embodiment, the case is described in which the present invention is applied to the X-ray imaging apparatus having the C-shaped arm 33 in which the imaging direction from the X-ray irradiation unit 31 to the flat panel detector 32 is changed relative to the examination table 1 and changing of the attaching position of the operation unit 17 to the top board 11 is particularly required. However, the present invention may be applied to an examination table 1 used in an X-ray imaging apparatus using other imaging methods.

DESCRIPTION OF REFERENCE SYMBOLS

1: examination table
2: storage unit
11: top board
12: first support unit
13: second support unit
14: third support unit
15: rail
16: cable
17: operation unit
18: operation region
19: support unit
20: shaft
21: lid
22: block member
23: plate member
24: hole portion
25: hole portion
26: winding member
31: X-ray generation unit
32: flat panel detector
33: C-shaped arm
34: slide unit
35: swivel unit
36: support unit
41: guide member
42: guide member

The invention claimed is:
1. A radiographic imaging apparatus comprising:
an examination table;
an operation unit
a radiation irradiation unit configured to irradiate radiation to a subject on the examination table; and
a radiation detection unit configured to detect the radiation irradiated from the radiation irradiation unit and transmitted through the subject,
wherein the examination table is provided with:
a top board configured to place the subject thereon;
a support unit configured to support the top board;
a top board moving mechanism configured to move the top board relative to the support unit;
a holding mechanism provided on at least one side of the top board and configured to hold the operation unit and
a storage unit provided adjacently to the top board and the storage unit including a space surrounded by upper and lower surfaces as well as side surfaces,
wherein a hole portion is provided on a side surface of the storage unit, and
wherein the support unit and the operation unit are connected to each other via a cable passing through the space and the hole portion.

2. The radiographic imaging apparatus as recited in claim 1,
   wherein the hole portion is formed in both side surfaces of the storage unit provided to the top board relative to a body axis of the subject.
3. The radiographic imaging apparatus as recited in claim 2,
   wherein a winding member capable of winding the cable is provided in the storage unit.
4. The radiographic imaging apparatus as recited in claim 3,
   wherein the holding mechanism comprises a rail arranged on both sides of the top board, and
   wherein the operation unit is attached to the top board via the rail.
5. The radiographic imaging apparatus as recited in claim 4,
   wherein the cable extends, from the operation unit to the storage unit, along the rail in a location that is substantially parallel and coplanar to the rail and the top board.
6. The radiographic imaging apparatus as recited in claim 3, further comprising:
   a C-shaped arm having an arcuate guide portion and supporting the radiation irradiation unit and the radiation detection unit;
   a slide mechanism slidably supporting the C-shaped arm by being engaged with the arcuate guide portion; and
   a rotation mechanism capable of rotatably supporting the C-shaped arm via the slide mechanism.

* * * * *